United States Patent
Gerecht et al.

(10) Patent No.: US 8,748,822 B1
(45) Date of Patent: Jun. 10, 2014

(54) CHIRPED-PULSE TERAHERTZ SPECTROSCOPY

(75) Inventors: Eyal Gerecht, Westminster, CO (US); David F. Plusquellic, Gaithersburg, MD (US); Kevin O. Douglass, Columbia, MD (US)

(73) Assignee: University of Massachusetts, Boston, MA (US)

( * ) Notice: Subject to any disclaimer, the term of this patent is extended or adjusted under 35 U.S.C. 154(b) by 162 days.

(21) Appl. No.: 13/346,999

(22) Filed: Jan. 10, 2012

Related U.S. Application Data

(60) Provisional application No. 61/498,729, filed on Jun. 20, 2011.

(51) Int. Cl.
    *G01J 5/02* (2006.01)
(52) U.S. Cl.
    USPC .................................................. 250/339.07
(58) Field of Classification Search
    USPC ............................ 250/339.01–339.09, 339.1, 250/339.11–339.15
    See application file for complete search history.

(56) References Cited

U.S. PATENT DOCUMENTS

| | | | |
|---|---|---|---|
| 5,939,721 A * | 8/1999 | Jacobsen et al. | 250/330 |
| 6,723,991 B1 * | 4/2004 | Sucha et al. | 250/341.1 |
| 6,747,736 B2 | 6/2004 | Takahashi | |
| 7,376,403 B1 | 5/2008 | Wanke et al. | |
| 7,473,898 B2 | 1/2009 | Holly et al. | |
| 7,687,773 B2 * | 3/2010 | Siegel et al. | 250/330 |
| 7,898,668 B2 | 3/2011 | Umetsu | |
| 8,035,083 B1 | 10/2011 | Kozlov et al. | |
| 8,269,971 B1 * | 9/2012 | Marsh et al. | 356/437 |
| 2003/0189711 A1 * | 10/2003 | Orr et al. | 356/484 |
| 2004/0081587 A1 * | 4/2004 | Melker et al. | 422/84 |
| 2006/0049356 A1 | 3/2006 | Shen et al. | |
| 2008/0317160 A1 * | 12/2008 | Tzeng et al. | 375/295 |
| 2011/0069309 A1 * | 3/2011 | Newbury et al. | 356/326 |
| 2013/0154611 A1 * | 6/2013 | Pate et al. | 324/76.19 |

OTHER PUBLICATIONS

U.S. Appl. No. 61/498,729, filed Jun. 20, 2011, entitled, "Chirped Pulse Fourier Transform Spectrocopy at Millimeter and THz Frequencies."
Gerecht, E. et al. "Chirped-pulse terahertz spectroscopy for broadband trace gas sensing," Optics Express, vol. 19, Issue 9, pp. 8973-8984 (2011).
Dian, B.C., "Measuring Picosecond Isomerization Kinetics via Broadband Microwave Spectroscopy," Science 320, 924-928 (2008).
Wild, W. "Terahertz heterodyne technology for astronomy and planetary science," 15th International Conference on Terahertz Electronics, Sep. 2-9, 2007, 323-325.
Uhm, W.-Y. et al., "A High Performance V-band Monolithic Quadruple Sub-harmonic Mixer," 2003 IEEE MTT-S Digest, vol. 2, 1319-1322.
Bigourd, D. et al., "Detection and quantification of multiple molecular species in mainstream cigarette smoke by continuous-wave terahertz spectroscopy," Optics Letters, vol. 31, No. 15, Aug. 1, 2006.

(Continued)

*Primary Examiner* — David Porta
*Assistant Examiner* — Taeho Jo
(74) *Attorney, Agent, or Firm* — Burns & Levinson LLP; Orlando Lopez

(57) ABSTRACT

Terahertz spectroscopy methods that are fast and have excellent spectral resolution and that do not require background correction of the instrument response without sample are disclosed. In one instance, the methods include phase coherent chirp pulse generation and phase coherent detection.

30 Claims, 10 Drawing Sheets

(56) References Cited

OTHER PUBLICATIONS

Ekstrom, H. et al., "Conversion Gain and Noise of Niobium Superconducting Hot-Electron Mixers," IEEE Trans. Microw. Theory Tech. 1995, vol. 43, 938-947.

Fililpovic, D.F., et al., "Double-Slot Antenna on Extended Hemispherical and Elliptical Silicon Dielectric Lenses," IEEE Trans. Microw. Theory Tech. 1993, vol. 41, 1738-1749.

Pilston, R.G., "A Long Path Gas Absorption Cell," J. Opt. Soc. Am., vol. 44, No. 7, (1954).

Qi, Y. et al., "Phase Correction of Fourier Transform Ion Cyclotron Resonance Mass Spectra Using MatLab," J. Am. Soc. Mass Spectrom. (2011).

Harmon, S.A., Part-per-million gas detection from long-baseline THz spectroscopy, Applied Physics Letters, vol. 85, No. 11, Sep. 13, 2004.

Hu, H. et al. "Reference Deconvolution, Phase Correction, and Line Listing of NMR Spectra by the 1D Filter Diagonalization Method," Journal of Magnetic Resonance 134, 76-87 (1998).

\* cited by examiner

CHIRPED-PULSE TERAHERTZ SPECTROSCOPY

CROSS REFERENCE TO RELATED APPLICATIONS

This application claims priority of U.S. Provisional Application Ser. No. 61/498,729, filed Jun. 20, 2011, entitled, "CHIRPED PULSE FOURIER TRANSFORM SPECTROCOPY AT MILLIMETER AND THz FREQUENCIES," which is incorporated by reference herein in its entirety for all purposes.

STATEMENT REGARDING FEDERALLY SPONSORED RESEARCH OR DEVELOPMENT

This invention was made with U.S. Government support from the Upper Atmospheric Research Program of the National Aeronautics and Space Administration under contract NNH09AK47I and the National Institute for Standards and Technology. The U.S. Government has certain rights in the invention.

BACKGROUND

These teachings relate generally to spectroscopy, and, more particularly, to sample sensing by terahertz spectroscopy.

Spectroscopy in the terahertz (THz) region is a highly sensitive technique for detecting the gas phase rotational spectrum of a vast number of small compounds that have permanent dipole moments. The terahertz region offers several distinct advantages: i) resolved spectral features for a wide range of species are accessible by the frequency coverage of a single source (currently having 50 GHz to 100 GHz of bandwidth), ii) complete selectivity is possible because of the small intrinsic spectral widths even in "noisy" or "dirty" environments, iii) optimal sensitivity is realized by probing near the peak of the thermal Boltzmann distribution, iv) absolute specificity is achieved since frequencies are traceable to the Rb atomic standard ($\pm 2$ parts in $10^{10}$), and v) absorption signals reflect absolute concentration without need of instrument calibration factors. In particular, rotational spectroscopy is sensitive to molecular structure, and each molecule (even isotopically substituted molecules) has a unique rotational spectrum much like a finger print or bar code. For molecules with only a few heavy atoms, the spectral region at 0.5 THz is near the peak of the Boltzmann distribution at room temperature and therefore, is the most sensitive region for detection of rotational lines. Many of these simple molecules are key atmospheric species ($N_2O$, $H_2O$), volatile organic compounds (formaldehyde, methanol), or indicators of disease states (NO, acetone). For direct absorption studies, the resolution is Doppler limited at room temperature to (1 to 5) MHz at 500 GHz for small molecules because of the thermal velocity distribution. The clear sensitivity advantages together with recent technological advances in sources and receivers make this region well suited for developing an analytical instrument for trace gas analysis.

A number of spectroscopic sensing THz systems using different technologies have demonstrated trace gas detection of different components over the last decade or so. Bigourd et. al. reported a sensor based on photomixing techniques to detect and quantify small quantities of hydrogen cyanide, carbon monoxide, formaldehyde, and water. At present, THz spectroscopy is performed by (i) scanning a high-resolution (1 MHz) narrow-band source with bolometric detection or (ii) time-domain spectroscopy in which a broad (3 THz) spectrum is obtained by measuring the time dependence of the electric field of the THz pulse followed by Fourier transform to the frequency domain. The first method has excellent spectral resolution but is limited in response time, while the second method is fast but has insufficient spectral resolution. Furthermore, these are direct absorption methods that require background correction of the instrument response without sample.

There is a need for terahertz spectroscopy methods that are fast and have excellent spectral resolution. There is also a need for terahertz spectroscopy methods that do not require background correction of the instrument response without sample.

BRIEF SUMMARY

The above expressed needs are met by the present teachings.

In one embodiment, the method of these teachings includes generating a phase coherent terahertz (THz) chirp pulse, coupling the phase coherent THz chirp pulse to gas in a gas cell, detecting Free Induction Decay (FID) induced in the gas by the phase coherent THz chirp pulse, the detection being phase coherent, and sensing the gas from the detection of the FID.

Other embodiments of the method of these teachings are also disclosed.

In one embodiment, the system of these teachings includes a terahertz chirped pulse source, a gas cell, the terahertz chirped pulse signal being coupled to the gas cell, the coupled terahertz chirped pulse causing Free Induction Decay (FID) emission from gas in the gas cell, a heterodyne terahertz receiver receiving the FID emission from the gas cell, the heterodyne terahertz receiver enabling obtaining FID spectrum of the FID emissions, the terahertz chirped pulse and the heterodyne terahertz receiver being phase coherent, an output component receiving output from the heterodyne terahertz receiver.

Other embodiments of the system of these teachings are also disclosed.

For a better understanding of the present teachings, together with other and further objects thereof, reference is made to the accompanying drawings and detailed description and its scope will be pointed out in the appended claims.

DETAILED DESCRIPTION

Figure 1A:
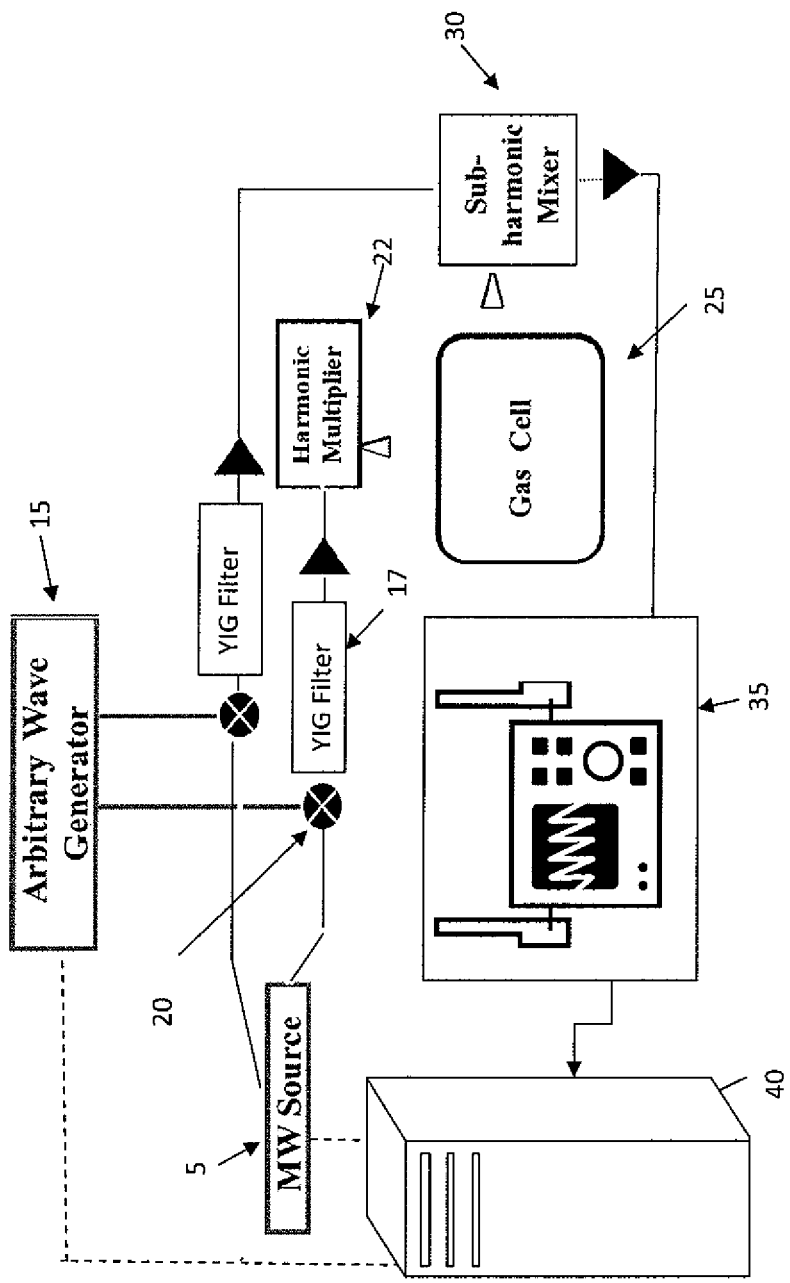
FIG. 1a depicts a schematic block diagram representation of one embodiment of the system of these teachings.

The following detailed description is of the best currently contemplated modes of carrying out these teachings. The description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range. However, any ranges not cited in the claims are only intended for illustration and not for limiting the range covered by our invention. Numerical values are cited for exemplary reasons and to identify embodiments and are not intended to limit the general concept of these teachings.

The terahertz (THz) range of frequencies, as used herein, includes frequencies from about 0.1 THz (100 GHz) to about 10 THz.

A "chirped pulse," as used herein, is a pulse in which the wavelength (or equivalently frequency) changes during the duration of the pulse.

Chirped pulse absorption (CPA), as used herein, refers to depletion of field amplitude in the chirped pulse when the frequency of radiation is on-resonance and when applied to a gas, liquid and/or solid samples.

Free Induction Decay (FID) emission, as used herein, refers to emission signals obtained by applying a pulse of radiation (shorter than the dephasing time) to a gas, liquid and/or solid samples and when the frequency of radiation is on-resonance, the pulse induces a macroscopic polarization state in the sample. Coherent emission from the sample is recorded in zero background after the pulse.

Embodiments of methods and systems for gas sensing by means of terahertz spectroscopy, where the methods are fast and have excellent spectral resolution and do not require background correction of the instrument response without sample, are disclosed herein below.

In one embodiment, the system of these teachings includes a terahertz chirped pulse source, a gas cell, the terahertz chirped pulse source being coupled to the gas cell, the coupled terahertz chirped pulse causing Free Induction Decay (FID) emission from gas in the gas cell, a heterodyne terahertz receiver receiving the CPA and/or FID emission from the gas cell, the heterodyne terahertz receiver enabling obtaining CPA spectrum and/or FID spectrum of the FID emissions, the terahertz chirped pulse and the heterodyne terahertz receiver being phase coherent over arbitrary number of repeated measurements defining a measurement period, an output component receiving output from the heterodyne terahertz receiver. In one instance, the terahertz chirped pulse source includes an arbitrary waveform generator, a synthesizer and a mixer. In another instance, the terahertz chirped pulse source also includes a sideband filter receiving an output from the mixer.

In another embodiment, the heterodyne terahertz receiver includes a local oscillator (LO).

LO sources at terahertz frequencies include far-infrared lasers operating on a number of discrete spectral lines throughout the terahertz spectrum, and harmonic multiplier sources in the lower terahertz spectrum. Harmonic multiplier sources are useful as LO sources because of their compact size, ease of use, and availability for frequencies at the lower terahertz spectrum. A multiplier source is driven by an oscillator with an output signal at a microwave frequency and may include, but is not limited to, a microwave synthesizer, phase locked dielectric resonance oscillator, or the upconverted output from an arbitrary waveform generator, and a multiplication chain to produce the THz frequency output. A typical harmonic multiplier source produces an output power of a few hundreds of µW, which is sufficient for a small focal plane array (FPA) of HEB devices operating in a heterodyne configuration. A frequency tunability of about 10% is achieved by replacing the low frequency signal, driving the multiplication chain, with a microwave synthesizer having sub-hertz spectral resolution. For the higher THz range, quantum-cascade lasers (QCLs) can be used.

In one instance, the system also includes a control component, wherein the control component (a) selects the terahertz chirp pulse and frequency of the local oscillator in order to detect the CPA and/or FID over a frequency range, and (b) switches, after detecting the CPA and/or FID over said frequency range, the terahertz chirp pulse and the frequency of the local oscillator in order detect the CPA and/or FID over another frequency range; the switching of the terahertz chirp pulse and the frequency of the local oscillator being performed substantially together and maintaining phase coherence in each frequency range. In another instance, the control component repeats steps (a) and (b) until the CPA and/or FID has been detected over a predetermined range of frequencies. In one embodiment, the control component includes at least one processor and computer usable media having computer readable code embodied therein, the computer readable code causing the at least one processor to perform steps in the method of these teachings. In one instance, the computer readable code causes the at least one processor to select the terahertz chirp pulse and frequency of the local oscillator in order to detect CPA and/or FID over a frequency range and switch, after detecting CPA and/or FID over said frequency range, the terahertz chirp pulse and the frequency of the local oscillator in order detect CPA and/or FID over another frequency range; the switching of the terahertz chirp pulse and the frequency of the local oscillator being performed substantially together and maintaining phase coherence from pulse-to-pulse in each frequency range to allow signal averaging of the electric field in the time domain.

In one instance, the system of these teachings also includes an analysis component receiving the output from the heterodyne terahertz receiver and comparing the output of the heterodyne terahertz receiver to predetermined spectra of gas components. The analysis component enables detection of the gas components. In one embodiment, the analysis component includes a Fast Fourier Transform component. In another embodiment, the analysis component performs a phase correction for line shapes of detected CPA and/or FID. In one embodiment, the analysis component includes at least one processor and computer usable media having computer readable code embodied therein, the computer readable code causing the at least one processor to perform the analyses disclosed herein above. In another embodiment, the analysis component and the control component are the same component.

In another instance, the system of these teachings also includes a frequency standard reference; the frequency standard reference being used in generating the terahertz chirped pulse and to phase lock a local oscillator used in the heterodyne terahertz receiver.

In one embodiment, the heterodyne terahertz receiver includes a hot electron bolometer (HEB). HEB devices have achieved receiver noise temperatures of about one order of magnitude less than Schottky barrier diode receivers, while requiring three to four orders of magnitude less LO power, a major advantage in the terahertz range in which it is still very difficult to produce high oscillator power. Schottky diodes respond directly to the LO and RF power that produce diode currents at THz frequencies. Detection and frequency conversion occur due to the nonlinearity of the I-V curve. Bolometers, and in particular hot electron bolometers (HEBs), on the other hand, respond to power, not to the high-frequency current (or voltage). This feature leads to devices that have very low parasitic reactance. The requirements for a high quality HEB device are for it to exhibit (1) a resistance that depends on the electron temperature in the bolometer medium, and (2) a short thermal time-constant, $\tau_{TH}$, which depends on how fast heat can be transferred from the heated electrons in the bolometer to a heat sink.

Different types of HEBs can be distinguished by the physical processes through which they dissipate the heat generated by the absorbed power. Phonon-cooled HEBs utilize a thin film of a superconductor such as NbN (see Ekström, H., Karasik, B., Kollberg, E., Yngvesson, K. S., "Conversion Gain and Noise of Niobium Superconducting Hot-Electron Mixers," *IEEE Trans. Microw. Theory Tech.* 1995 43, 938-947, which is incorporated by reference herein in its entirety for all purposes), and achieve IF bandwidths of about 5 GHz. An operating temperature range for the NbN HEB devices of 4 K to about 6 K is an advantage over most other far-infrared (FIR) devices, which require cooling to sub-kelvin temperatures.

In one embodiment, coupling the FID emission and output of the local oscillator to the detector comprises quasi-optical coupling. Quasi-optical systems have been developed to achieve guiding and coupling of THz radiation. Many THz detectors now use quasi-optical coupling to the incoming radiation field by use of a combination of dielectric lenses and integrated monolithic antennas. FIG. 1d shows a twin-slot antenna structure that is fabricated at the terminals of a HEB heterodyne detector. The twin-slot antenna has a highly symmetrical and linearly polarized radiation pattern and provides excellent power coupling to the incident Gaussian beam (see, for example, Filipovic, D. F., Gearhart, S. S., Rebeiz, G. M., "Double-Slot Antenna on Extended Hemispherical and Elliptical Silicon Dielectric Lenses," *IEEE Trans. Microw. Theory Tech.* 1993, vol. 41, 1738-1749, which is incorporated by reference herein in its entirety for all purposes). In the embodiment shown, not a limitation of these teachings, the terahertz signals couple to the device through an elliptical silicon lens 7 (a typical lens has a diameter of a few mm). The lens is a rotational ellipsoid that functions as an aperture antenna, and hence reshapes the far-field radiation pattern. The radiation from the twin slot antenna 11, placed at the second focus of the elliptical lens, becomes substantially a plane wave in the aperture plane outside the lens. In one instance, the combination of the silicon lens and the twin-slot antenna produces a far-field beam with a full-width half-power (FWHP) of about 3 degrees.

In another embodiment, the heterodyne terahertz receiver is a sub-harmonic heterodyne terahertz receiver (also referred to as having a sub-harmonic mixer). In one instance, the sub-harmonic heterodyne terahertz receiver includes a Schottky barrier diode detector.

Figure 1B:
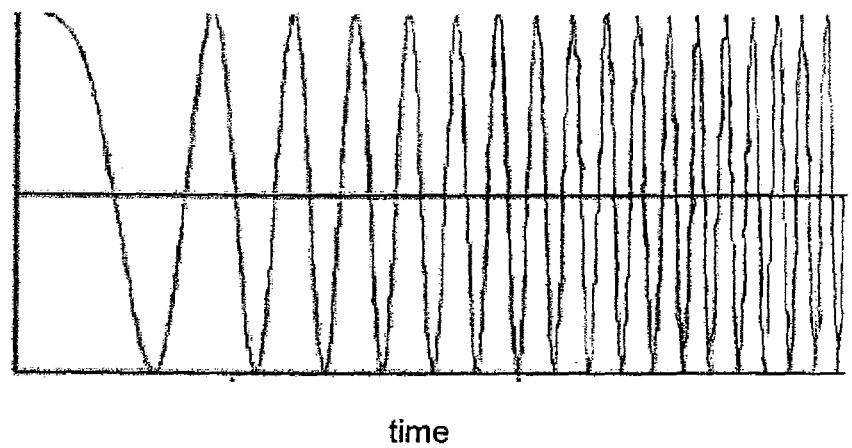
FIG. 1b shows one example of a chirped terahertz pulse as used in embodiments of the system of these teachings.
Figure 1C:
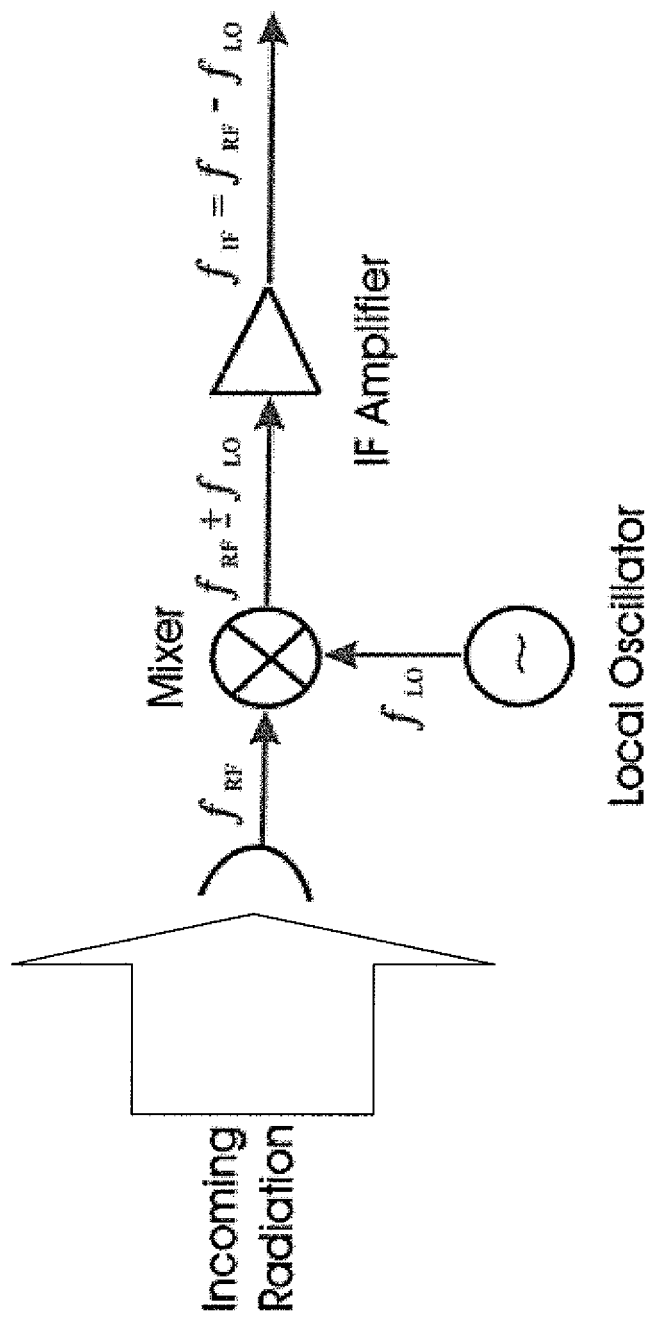
FIG. 1c shows a schematic graphical representation of a heterodyne receiver as used in embodiments of the system of these teachings.
Figure 1D:
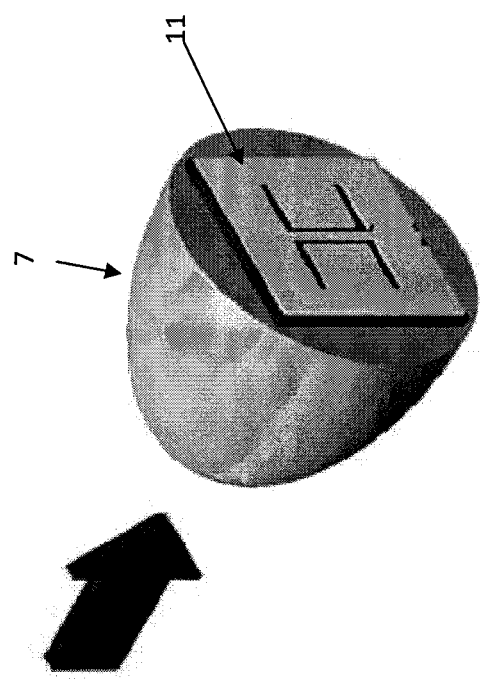
FIG. 1d shows a schematic graphical representation of a component used in embodiments of the system of these teachings.

FIG. 1a depicts one embodiment of the system of these teachings. Referring to FIG. 1a, a chirped pulse is generated by an arbitrary wave generator 15. (A chirped pulse is illustrated in FIG. 1b.) The chirped pulse is mixed (at a first mixer 20) with a microwave signal from a microwave source 5, filtered, in one instance by a YIG filter 17, and the filter signal is provided to an amplifier multiplier chain (also referred to as a harmonic multiplier) 22. The output of the harmonic multiplier 22 is coupled to the gas cell 25. The FID emissions from the gas cell are coupled to a sub harmonic mixer 30. A local oscillator signal, produced by mixing the microwave signal from the microwave source 5 with a non-chirped output of the arbitrary wave generator 15 and subsequently filtering and amplifying, is also provided to the sub-harmonic mixer 30. The local oscillator and the sub-harmonic mixer 30 and an IF amplifier provide sub-harmonic heterodyne detection (also referred to as a sub-harmonic heterodyne receiver). The chirped-pulse Fourier transform technique, implemented by the embodiment shown in FIG. 1a, requires that phase information be preserved over the entire bandwidth and for repeated chirped pulse measurements over the full measurement period. The sub-harmonic heterodyne detection is illustrated in FIG. 1c. The output of the sub-harmonic heterodyne receiver is provided to an output component (an oscilloscope in the embodiment shown) 35. The output is also provided to an analysis component 40. In the embodiment shown the analysis component is a computer system that also can be used as a control component.

In the terahertz system of these teachings, the chirped signal is directly coupled to the gas in the gas cell without need for a free jet-cooled expansion of the gas while, in a microwave spectrometer, the sample undergoes a free jet expansion into the active region using a pulsed nozzle typically operated at a 10 Hz pulse rate. Also, the terahertz system of these teachings requires that phase information be preserved over the entire bandwidth and for repeated chirped pulse measurements over the full measurement period.

Figure 2:
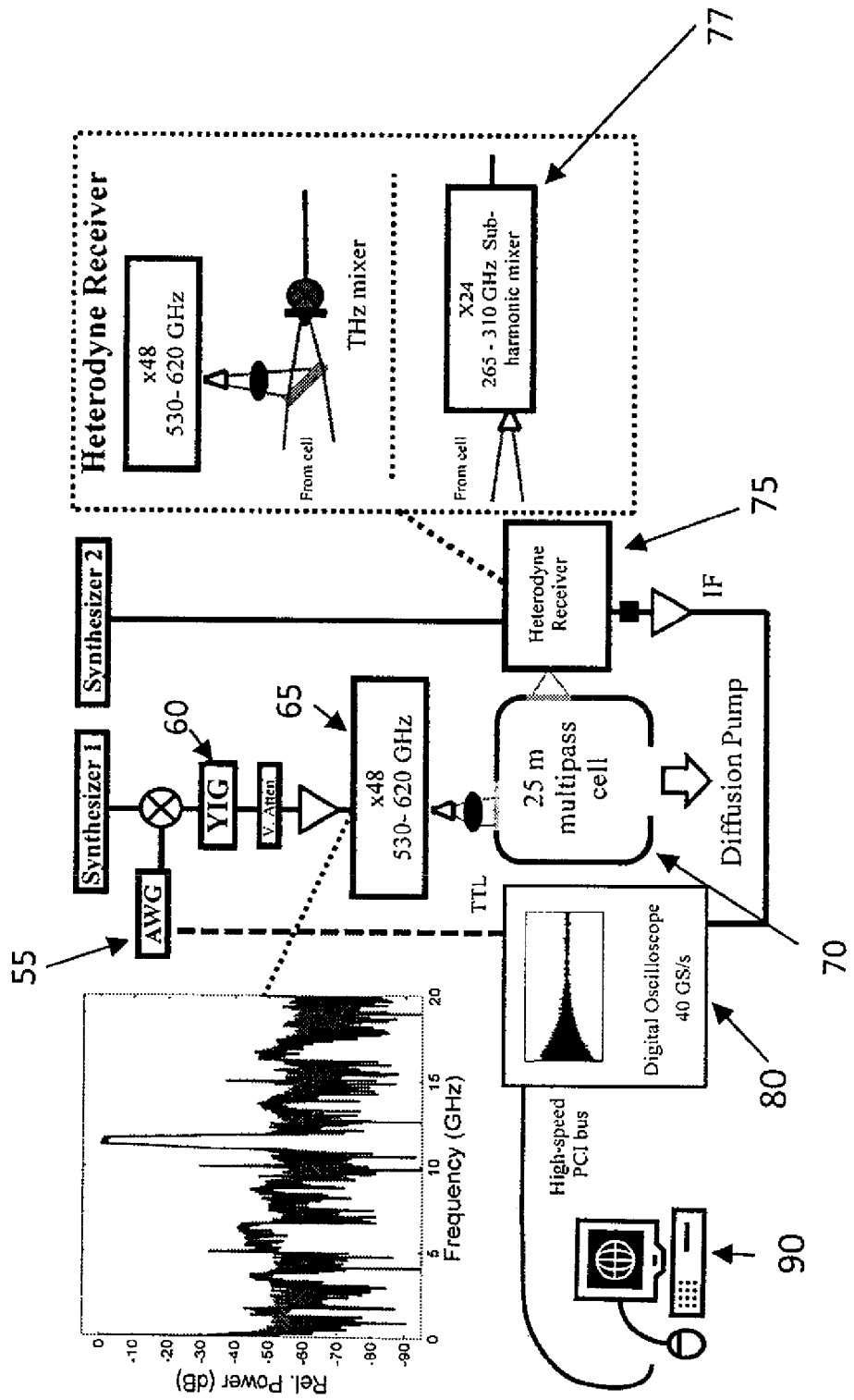
FIG. 2 is a schematic block diagram representation of one exemplary embodiment of the system of the teachings.

An exemplary embodiment is shown in FIG. 2. It should be noted that these teachings are not limited to this exemplary embodiment. Exemplary embodiments are shown in order to further elucidate these teachings. Since the exemplary embodiments are shown in order to elucidate specific instances or portions of these teachings, some of the exemplary embodiments may not include all the components of the system. In the exemplary embodiment shown in FIG. 2, the chirped pulses were digitally generated in a 12 GS/s arbitrary waveform generator 55 (AWG) (Tektronix, AWG7221C, in this exemplary embodiment). The AWG was programmed with a 25 ns long chirped pulse centered at 2.4 GHz that covers a bandwidth of 200 MHz. The initial and final 5 ns of the pulse were dampened to zero using a raised cosine function to minimize sinx/x modulation. The AWG signal was mixed with a microwave Synthesizer 1 at 9.075 GHz, filtered and then amplified before entering the ×48 amplifier multiplier chain (AMC) 65. Filtering was achieved using a tunable bandpass yttrium iron garnet (YIG) filter 60 to select only the upper sideband of the mixer output. The carrier and lower sideband were suppressed by approximately 40 dB. The output of the AMC was a chirped-pulse signal from (546 to 555.6) GHz. Any portion of the entire multiplier chain bandwidth from (530 to 620) GHz can easily be accessed by tuning the AWG and filter at a speed currently limited by the 1 GHz/ms sweep rate of the YIG filter. The THz chirped pulse was then coupled into 25 meter long absorption cell and then into a sub-harmonic mixer AMC (Mix-AMC) 77 (included in heterodyne receiver 75) for detection. A long path (multipass) absorption cell 70 (also known as a White cell, see R. G. Pilston, J. U. White, "A Long Path Gas Absorption Cell," J. Opt. Soc. Am., Vol. 44, No. 7, (1954), which is incorporated by reference herein is entirety for all purposes) is used.

The heterodyne detector 75 mixes the CPA and/or FID signals from the gas cell against the local oscillator signal, producing a signal of the different frequency, referred to as the intermediate frequency (IF) signal. In the above exemplary embodiment, the CPA and/or FID signals are 530 GHz, the local oscillator signal is 520 GHz and the IF signal is 10 GHz. In the above exemplary embodiment, a Schottky barrier diode (SBD) is used as a mixer. The SBD allows room temperature operation at the expense of some sensitivity and high local oscillator signal power requirements. The complex quasi-optical alignment and high local oscillator signal power requirements can be ameliorated by use of a sub harmonic heterodyne detector. In the sub harmonic heterodyne detector, the fixed frequency local oscillator signal is generated at about half the chirped pulse frequency coupled directly into the SBD and then mixed together with the CPA and/or FID signals on the SBD. In the above exemplary embodiment, the mixing again results in an IF signal of 10 GHz, which removes the high power requirement at 530 GHz.

In this exemplary embodiment, the Mix-AMC down-converted the signal with a fixed local oscillator (LO) set to 545.760 GHz (the frequency of Synthesizer 2×48) to produce an intermediate frequency (IF) signal from (0.2 to 9.8) GHz. The IF was amplified by 42 dB and digitized on the oscilloscope 80 (LeCroy 8zi, in the embodiment shown) at a sampling rate of 20 GS/s (2 times the Nyquist limit) for a duration of 4 ms (8 000 sample records of 500 ns each). The 25 ns pulse was digitized to record the CPA and the remaining 475 ns of the interval was used to record the FID signals. The repetition rate of the waveform generator was set to 2 MHz. The output of the oscilloscope is provided to an analysis computer/control component 90 via high throughput PCI interface. The analysis computer/control component 90 can a) select the terahertz chirp pulse and frequency of the local oscillator in order to detect the CPA and/or FID over a frequency range, and (b) switch, after detecting the FID over said frequency range, the terahertz chirp pulse and the frequency of the local oscillator in order detect the FID over another frequency range.

Figure 3:
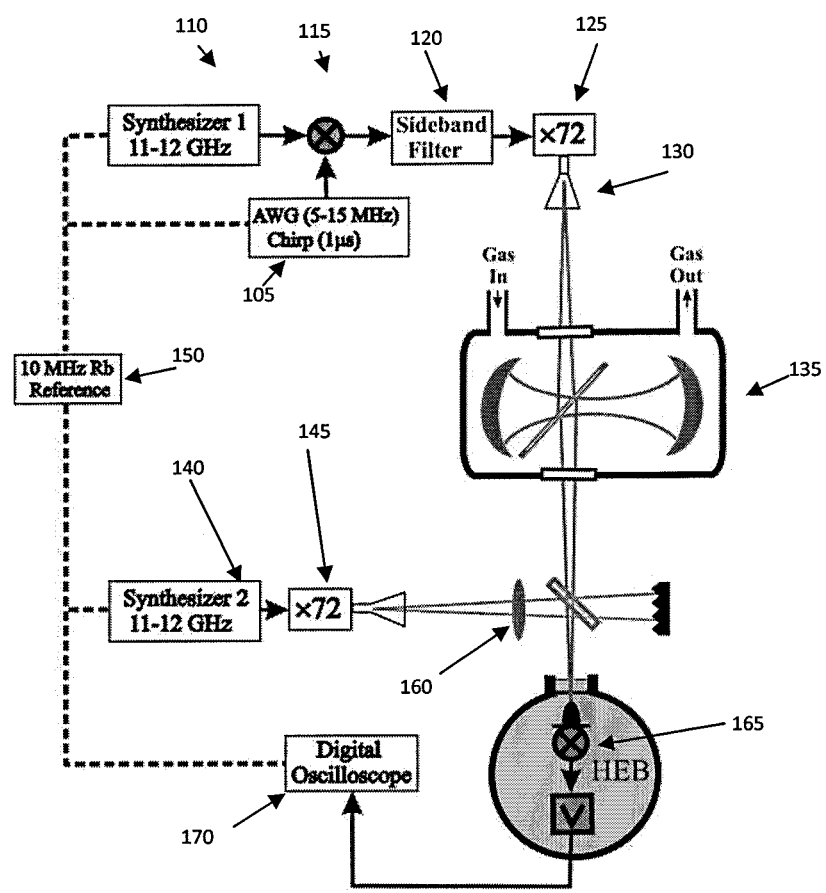
FIG. 3 is a schematic block diagram representation of another exemplary embodiment of the system of the teachings.

Another exemplary embodiment is shown in FIG. 3. In the exemplary embodiment shown in FIG. 3, a chirped pulse at MHz to GHz frequencies is digitally synthesized by the arbitrary function generator (AWG) 105. The chirped pulse is upconverted to the microwave (MW) region by combining this output with MW synthesizer 1 (110) in a high bandwidth solid state mixer 115. The lower sideband (MW minus chirp) and the carrier are removed using a YIG filter 120 and the output is frequency multiplied by 72 (125, FIG. 3) to produce a chirped pulse at THz frequencies. The pulse duration is about ~1 μs with repetition rates ranging from 10 kHz to 500 kHz. The power level across the chirped pulse is ~100 μW.

The multiplier output is directed by a horn 130 to the input mirror of a multi-pass cell 135 or to a beam splitter for coupling to a high-Q cavity. Room temperature gas continuously flows through the chamber at reduced pressure (<0.1 kPa). For the high-Q cavity, the beam splitter also couples the emission signal out to the HEB. The beam splitter and other loss mechanisms ultimately determine the cavity Q.

The local oscillator (LO) for the heterodyne detection is created using synthesizer 2 (140, FIG. 3) and a second frequency multiplier 145. All active components are phase locked to a 10 MHz rubidium frequency standard reference 150. The LO frequency is offset by 500 MHz above (or below) the chirped frequency range. The LO and coherent emission signal are combined using a beam splitter and focused onto the quasi-optically coupled HEB 165 with a silicon lens 160. The HEB mixer output is at the difference frequency (IF) of the coherent emission signal and LO. The IF signal is amplified and recorded by a digital oscilloscope 170 for a duration determined by the $T_2$ dephasing time of the gas (<1 μs) at reduced pressure (<100 mTorr).

In one embodiment, the method of these teachings includes generating a phase coherent terahertz (THz) chirp pulse, coupling the phase coherent THz chirp pulse to gas in a gas cell, detecting the chirped pulse absorption (CPA) and Free Induction Decay (FID) induced in the gas by the phase coherent THz chirp pulse, the detection being also phase coherent over the full measurement period, and sensing the gas from the detection of the CPA and FID. In one instance, the step of sensing the gas comprises identifying gas components by comparing detected CPA and/or FID spectra to predetermined component spectra. In embodiments of the method of these teachings, the phase information is preserved over the entire bandwidth and for repeated chirped pulse measurements over the full measurement period (up to hours in duration).

In one instance, detecting CPA and/or FID comprises detecting by coherent heterodyne detection of CPA and/or FID. In another instance, detecting CPA and/or FID comprises detecting by coherent sub-harmonic heterodyne detection of CPA and FID.

In one instance, generating a phase coherent chirp pulse and detecting by coherent heterodyne detection comprise using a frequency standard reference in generating the phase coherent chirp pulses and to phase lock a local oscillator used in the phase coherent heterodyne detection.

In one embodiment, detecting CPA and/or FID comprises coupling the CPA and/or FID emission to a heterodyne detector by quasi-optical coupling methods. In one instance, the gas cell is a multipass gas cell.

In another instance, a local oscillator is used in the phase coherent heterodyne detection. In yet another instance, the method also includes a) selecting the THz chirp pulse and frequency of the local oscillator in order to detect FID over a frequency range and b) switching, after detecting CPA and/or FID over the frequency range, the THz chirp pulse and the frequency of the local oscillator in order detect CPA and/or FID over another frequency range, the switching of the THz chirp pulse and the frequency of the local oscillator being performed substantially together and maintaining phase coherence. In a further instance, steps (a) and (b) are repeated until CPA and/or FID has been detected over a predetermined range of frequencies.

In another embodiment, the method also includes phase correcting line shapes of detected CPA and/or FID.

In another embodiment, the method of these teachings includes generating a phase coherent terahertz (THz) chirp pulse, coupling the phase coherent THz chirp pulse to a liquid and/or solid material, detecting the chirped pulse absorption (CPA) and/or Free Induction Decay (FID) induced in the liquid and/or solid by the phase coherent THz chirp pulse, the detection being also phase coherent over the full measurement period, and sensing the liquid and/or solid from the detection of the CPA and/or FID. In one instance, the step of sensing the liquid and/or solid comprises identifying components by comparing detected CPA and/or FID spectra to predetermined component spectra. In embodiments of the method of these teachings, the phase information is preserved over the entire bandwidth and for repeated chirped pulse measurements over the full measurement period.

In one embodiment, the method of these teachings for enabling averaging/subtraction of detected terahertz (THz) signals includes generating phase coherent terahertz (THz) chirp pulses, phase coherence being maintained between repeated terahertz (THz) chirp pulses in the frequency range of the chirped pulse and detecting THz signals generated by coupling the phase coherent THz chirp pulse to a sample, where the detection is phase coherent and repeated chirped pulse measurements are phase coherent. The maintained phase coherence enables coherently averaging/subtracting of the generated THz signals. In one instance, phase coherence is maintained by using a frequency standard reference in generating the phase coherent chirp pulses and to phase lock a local oscillator used in phase coherent heterodyne detection. The method of these teachings for enabling average/subtraction of detected terahertz (THz) signals has several advantages over the conventional methods. While in some conventional methods the pulse generation (such as fast pulses) can be made coherent with the detection, repeated pulses are not enforced to be coherent with each other and the repeated measurements are not enforced to be coherent. Averaging over many or long periods of generated signals is difficult or not as accurate as required in those conventional methods.

An exemplary embodiment of the practice of the method of these teachings, using the embodiment of the system as shown in FIG. 2, is presented below. It should be noted that these teachings are not limited to this exemplary embodiment. Exemplary embodiments are presented in order to further elucidate these teachings.

In the exemplary embodiment, a gas mixture containing five different components was made from premixed gas cylinders or from the pure vapor above liquid samples and mixed directly in the White cell. Table 1 lists the composition of the gas mixture as determined using a thermistor pressure sensor. The total pressure used for these measurements was 7.0 Pa (53 mTorr).

Figure 4:
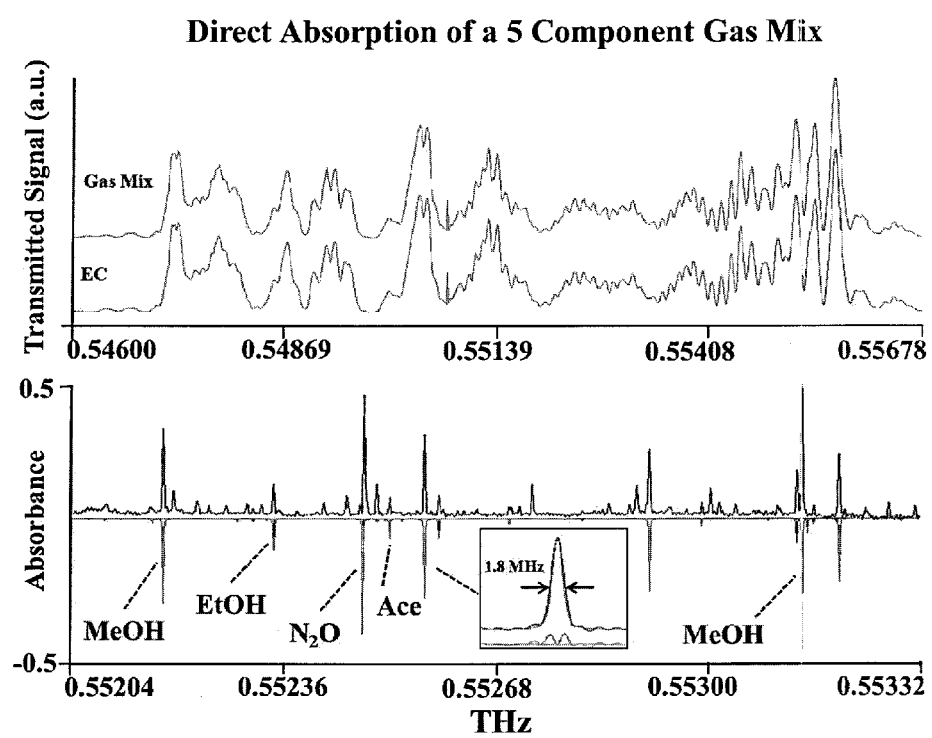
FIG. 4 shows results from one embodiment of the method and system of these teachings.
Figure 5:
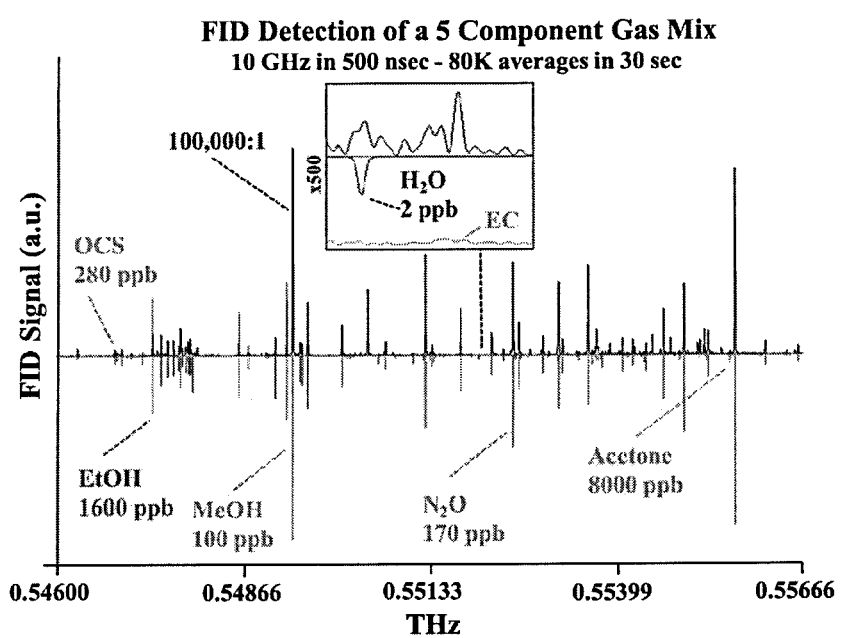
FIG. 5 shows results on the application of one step in one embodiment of the method of these teachings.

Separate sets of measurements of the chirped pulse absorption (CPA) and free induction decay (FID) signals were performed on the gas mixture shown in Table 1. To obtain the best signal-to-noise (S/N) ratios for FID, the dynamic range of the 8 bit digitizer at the oscilloscope is maximized for small signal detection by increasing the input sensitivity by 10-fold. However, simultaneous measurement of the CPA and FID can be performed using an IF splitter and additional amplifier for the IF. As with CPA, the FFT was taken of the averaged time domain electric field amplitude with and without gas in the cell and the resulting magnitude was squared to give intensity. The CPA and/or FID spectra obtained from the FFT of an 80 000 record average acquired in 30 seconds is shown in FIGS. 4 and 5. It is also noted that the real data throughput possible is 750 times faster and currently limited by the speed of the oscilloscope.

FIG. 4 shows the measured CPA spectrum of the five component gas mixture over a 10 GHz bandwidth. Predictions from HITRAN and JPL (Jet Propulsion Laboratory) databases are shown inverted and below the measured spectrum. The precise time of each absorption feature relative to the trigger source is less than 5 ps.

FIG. 5 shows the measured FID spectrum of the five component gas mixture over a 10 GHz bandwidth. Predictions from HITRAN and JPL (Jet Propulsion Laboratory) databases are shown inverted and below the measured spectrum. The insert shows a 45 MHz section containing the $1_{10} \leftarrow 1_{01}$ transition of the $H_2^{17}O$ isotopologue at 552.020 GHz and the corresponding signal obtained when the cell was evacuated using a diffusion pump (EC). The parent isotopologue of this transition at 556.837 GHz is saturated (2773 times stronger) and not shown.

Since the FID signals are detected in the absence of chirp pulse, this method is no longer limited in sensitivity by power and/or phase variations in the ratio between the signal and background signals. The dominant source of noise following the chirp is a 200-fold attenuated copy of the chirp (echo) that is time delayed by 167.55 ns. This delay corresponds to a pathlength of 50.23 m or roughly twice the optical pathlength of the White cell. A misaligned or scattered portion of the chirp that is inadvertently coupled into the 50 m (80 pass) configuration of the White cell is the likely cause of this source of noise. However, because both the empty cell and gas filled cell measurements are phase coherent, direct subtraction of these time domain waveforms eliminates the echo and other spurious signals and enables true background free signals to be Fourier transformed to the frequency domain in the most efficient way possible. Following subtraction, most of the 475 ns region available for FID detection is recovered.

TABLE 1

Summary of Multi-Component Gas Composition and Detection Sensitivities in Absorption (ABS NEC) and Emission (FID NEC) for a 7 Pa (53 mTorr) gas sample. Uncertainties are type B (k = 1) and are shown for the least significant digit.

| Molecule | Pressure/ Pa$^{MIX}$ | Pressure/ Pa [mTorr]$^{ABS}$ | % | ABS NEC/ ppm$^a$ | FID NEC/ ppb$^a$ | $\Delta V_L$: $\Delta V_G$/ MHz |
|---|---|---|---|---|---|---|
| MeOH | 2.0(8) | 0.49(4) [3.7(3)] | 7.0(6) | 470 | 100 | 0.53:1.20 |
| $N_2O$ | 0.27(9) | 0.27(3) [2.0(2)] | 3.8(1) | 370 | 170 | 0.32:1.03 |
| OCS (Carbonyl sulfide) | 0.01(5) | 0.066(4) [0.50(3)] | 0.94(6) | 100 | 280 | 0.36:0.87 |
| EtOH | 2.0(3) | — | 28(4) | 4000 | 1600 | 0.5$^c$:0.99 |
| Acetone | 1.7(3) | — | 25(3) | 7000 | 8000 | 0.5$^c$:0.88 |
| $H_2O$ | trace | 0.003(2) [0.02(1)] | 0.04(2) | — | 2$^b$ | 0.43:1.61 |

$^a$NEC is noise equivalent concentration as determined from the gas concentration and the signal-to-noise ratio of the strongest line in the 10 GHz region. 1 ppm = 1 part in $10^6$ parts and 1 ppb = 1 part in $10^9$ parts.
$^b$NEC is estimated for strong water line at 556.936 GHz based on ratio of transition strengths (x2773) relative the 552.021 GHz line (see FIGS. 4 and 5).
$^c$Estimated based on absorption line shape.

Figure 6:
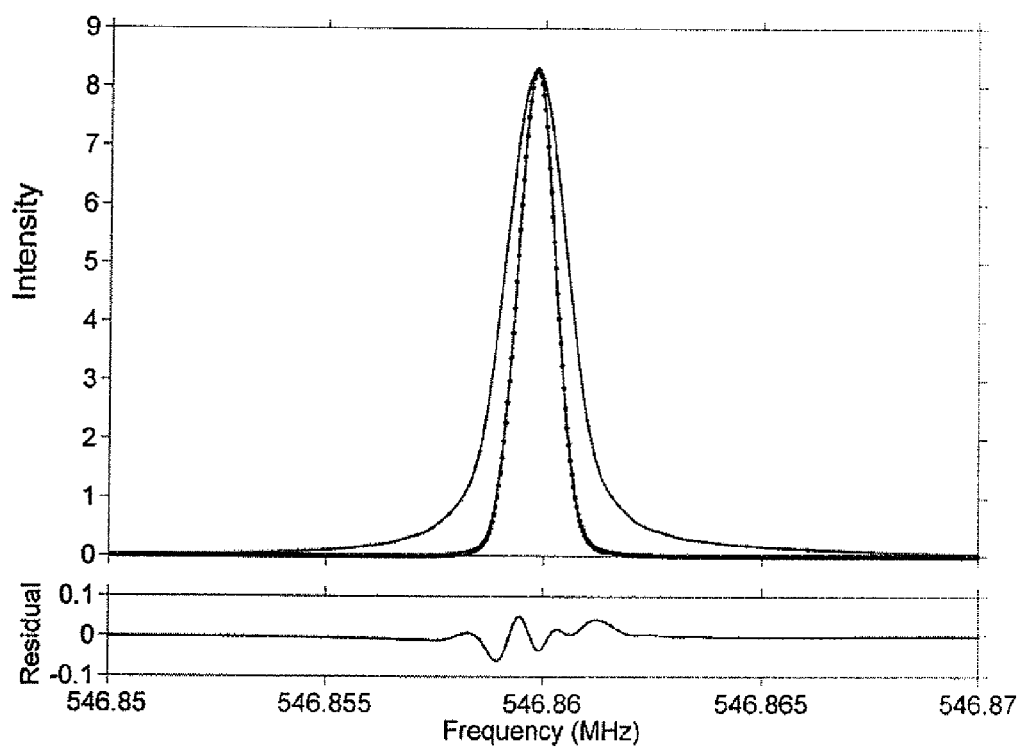
FIG. 6 shows results on the application of one step in one embodiment of the method of these teachings.

The line width parameters may be obtained directly from the time domain signals and/or from line shapes observed in the FID spectrum. The Voigt line widths of the squared magnitude spectrum includes contributions from absorption (imaginary part of the FFT) and dispersion (real part of the FFT) and will always be broader than the square of the absorption part alone. As is conventional in NMR and Fourier-transform ion cyclotron resonance (FT-ICR), narrower line widths are achieved only after phase correcting the imaginary component of the Fourier transform. The phase correcting procedure (see, for example, Yulin Qi et al., Phase Correction of Fourier Transform Ion Cyclotron Resonance Mass Spectra Using MatLab, J. Am. Soc. Mass Spectrom. (2011), which is incorporated by reference herein in its entirety and for all purposes) has been applied to the line shape of OCS shown in FIG. 6. As shown therein, the square of the imaginary part of the FID provides an accurate measure of the Voigt line shape parameters reported in the HITRAN (High-Resolution Transmission molecular absorption database) database. Significant narrowing is also expected for the phase corrected FID data shown in FIG. 5. However, at higher pressures, the effect of line narrowing will become more subtle as the Lorentzian line shape component becomes dominant.

The method of these teachings can find numerous applications, the applications arising from the source of the gas. The method of these teachings enables monitoring of trace species in a non-destructive and non-invasive manner. Some of the possible applications of the method of these teachings include, but are not limited to,

- detection of Toxic Industrial Chemicals (TICs) and Toxic Industrial Materials (TIMs) in the presence of multiple interferents with low false alarm rates for homeland defense,
- human breath analysis to aid medical diagnoses in clinical, triage, emergency, and surgical units,
- greenhouse gas emission monitoring to facilitate accurate assessments of carbon emission impact on global climate change and carbon mitigation,
- ion and radical concentration profiling in chemical vapor deposition and etching processes to advance materials engineering and nanofabrication, and
- research on biomolecules to improve the predictive accuracy of models used to enhance drug efficacy and discovery.

Figure 7:
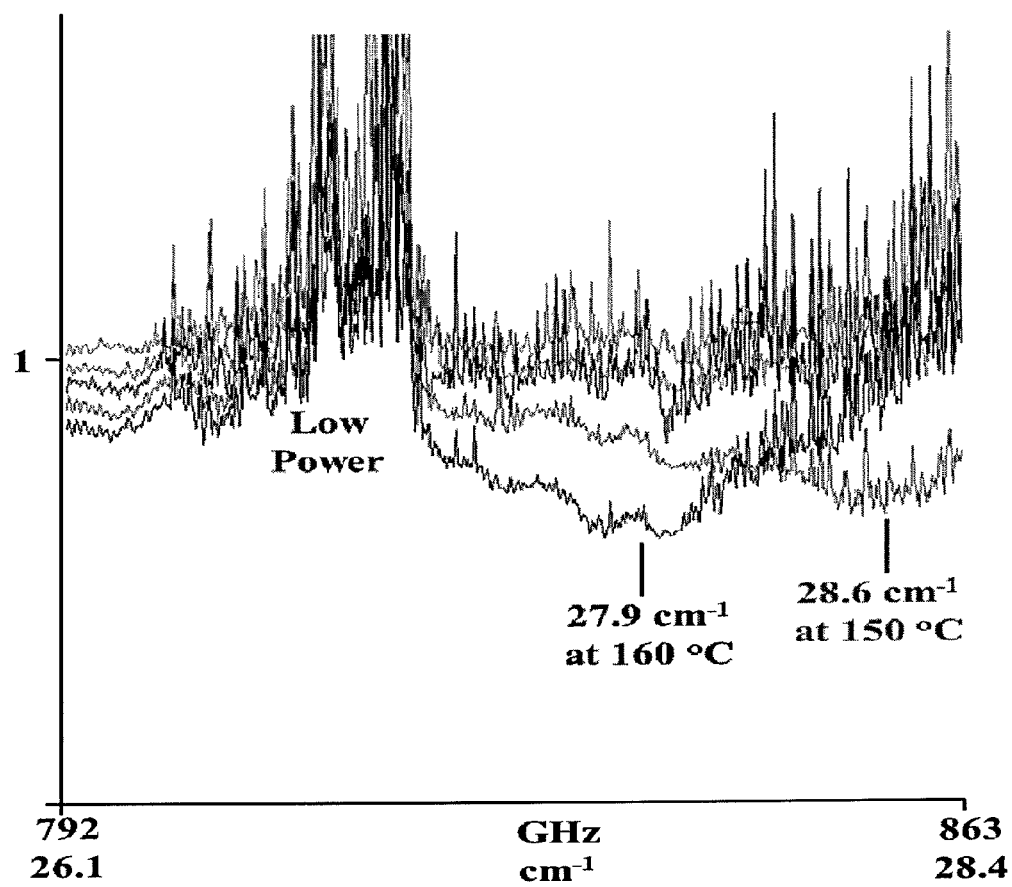
FIG. 7 shows results on the application of one step in one embodiment of the method of these teachings.

In another exemplary embodiment, a solid sample consisting of nickel oxide was placed between the THz chirped pulse source and heterodyne detector. FIG. 7 shows the measured CPA spectra of the solid nickel oxide between 792 GHz and 863 GHz and at five different temperatures. The anti-ferromagnetic resonance absorption at 160 C is easily observed during a total measurement time of 2 ms.

The present teachings allow measurement of the spectra of molecules that were not previously measured at the THz frequency range.

Although the invention has been described with respect to various embodiments, it should be realized these teachings are also capable of a wide variety of further and other embodiments within the spirit and scope of the appended claims.

What is claimed is:

1. A method for gas sensing, the method comprising:
   generating phase coherent terahertz (THz) chirp pulses;
   coupling the phase coherent THz chirp pulse to gas in a gas cell; detecting Free Induction Decay (FID) induced in the gas by the phase coherent THz chirp pulse;
   the phase coherent terahertz (THz) chirp pulses being phase coherent with a receiver used in detection; the receiver and a terahertz (THz) chirp pulse being phase locked using a frequency standard reference; and
   sensing the gas from the detection of the FID.

2. The method of claim 1 wherein the step of sensing the gas comprises identifying gas components in a mixture by comparing detected FID spectrum to predetermined component spectra.

3. The method of claim 2 wherein the predetermined component spectra comprises toxic chemicals and toxic material spectra; and wherein the method further comprises determining whether toxic chemicals and/or toxic materials are present.

4. The method of claim 2 wherein the gas is provided by breath from a living organism; wherein the predetermined spectra comprises spectra from predetermined biomarkers; and wherein the method further comprises providing data for medical diagnosis.

5. The method of claim 2 wherein the gas is obtained from greenhouse gas emissions.

6. The method of claim 2 wherein the predetermined spectra comprises spectra from trace gas components.

7. The method of claim 1 wherein detecting FID comprises detecting by coherent heterodyne detection of FID.

8. The method of claim 7 wherein detecting FID comprises detecting by coherent sub-harmonic heterodyne detection of FID.

9. The method of claim 7 wherein generating a phase coherent chirp pulse and detecting by coherent heterodyne detection comprise using a frequency standard reference in generating the phase coherent chirp pulses and to phase lock a local oscillator used in the phase coherent heterodyne detection.

10. The method of claim 7 wherein detecting FID comprises coupling the FID emission to a heterodyne detector by quasi-optical coupling methods.

11. The method of claim 1 further comprising phase correcting line shapes of detected FID.

12. The method of claim 1 wherein the gas cell is a multi-pass gas cell.

13. A method for gas sensing, the method comprising:
   generating phase coherent terahertz (THz) chirp pulses;
   coupling the phase coherent THz chirp pulse to gas in a gas cell; detecting Free Induction Decay (FID) induced in the gas by the phase coherent THz chirp pulse;
   the detection being phase coherent; and
   sensing the gas from the detection of the FID;
   wherein detecting FID comprises detecting by coherent heterodyne detection of FID; and
   wherein a local oscillator is used in the phase coherent heterodyne detection; and
   wherein the method further comprises:
   a) selecting the THz chirp pulse and frequency of the local oscillator in order to detect FID over a frequency range; and
   b) switching, after detecting FID over said frequency range, the THz chirp pulse and the frequency of the local oscillator in order detect FID over another frequency range; the switching of the THz chirp pulse and the frequency of the local oscillator being performed substantially together and maintaining phase coherence.

14. The method of claim 13, further comprising repeating steps (a) and (b) until FID has been detected over a predetermined range of frequencies.

15. A system for chirped pulse terahertz spectroscopy, the system comprising:
   a terahertz chirped pulse source;
   a gas cell; the terahertz chirped pulse source being coupled to the gas cell;
   the coupled terahertz chirped pulse causing Free Induction Decay (FID) emission from gas in the gas cell;
   a heterodyne terahertz receiver receiving the FID emission from the gas cell; the heterodyne terahertz receiver enabling obtaining FID spectrum of the FID emissions;

the terahertz chirped pulse and the heterodyne terahertz receiver being phase coherent;

an output component receiving output from the heterodyne terahertz receiver;

and a frequency standard reference; the frequency standard reference being used in generating the terahertz chirped pulse and to phase lock a local oscillator included in the heterodyne terahertz receiver.

16. The system of claim 15 further comprising an analysis component receiving the output from the heterodyne terahertz receiver and comparing the output of the heterodyne terahertz receiver to predetermined spectra of gas components; the analysis component enabling detection of the gas components.

17. The system of claim 16 wherein the analysis component includes a Fast Fourier Transform component.

18. The system of claim 16 wherein the analysis component performs a phase correction for line shapes of detected FID.

19. The system of claim 15 wherein the gas cell is a multipass gas cell.

20. The system of claim 15 wherein the heterodyne terahertz receiver comprises a hot electron bolometer.

21. The system of claim 15 wherein the terahertz chirped pulse source comprises:
an arbitrary waveform generator;
a synthesizer; and
a mixer.

22. The system of claim 21 wherein the terahertz chirped pulse source further comprises a sideband filter receiving an output from the mixer.

23. The system of claim 15 wherein coupling the FID emission and output of the local oscillator to the detector comprises quasi-optical coupling.

24. The system of claim 15 wherein the heterodyne terahertz receiver is a sub-harmonic heterodyne terahertz receiver.

25. The system of claim 24 wherein the sub-harmonic heterodyne terahertz receiver comprises a Schottky barrier diode detector.

26. The system of claim 15 further comprising a control component, wherein the control component (a) selects the terahertz chirp pulse and frequency of the local oscillator in order to detect FID over a frequency range, and (b) switches, after detecting FID over said frequency range, the terahertz chirp pulse and the frequency of the local oscillator in order detect FID over another frequency range; the switching of the terahertz chirp pulse and the frequency of the local oscillator being performed substantially together and maintaining phase coherence.

27. The system of claim 26 wherein the control component repeats steps (a) and (b) until FID has been detected over a predetermined range of frequencies.

28. The system of claim 26 wherein the control component comprises:
at least one processor; and
computer usable media having computer readable code embodied therein, the computer readable code causing said at least one processor to:
a) select the terahertz chirp pulse and frequency of the local oscillator in order to detect RD over a frequency range; and
b) switch, after detecting FID over said frequency range, the terahertz chirp pulse and the frequency of the local oscillator in order detect FID over another frequency range; the switching of the terahertz chirp pulse and the frequency of the local oscillator being performed substantially together and maintaining phase coherence.

29. A method for enabling averaging/subtraction of detected terahertz (THz) signals, the method comprising:
generating phase coherent terahertz (THz) chirp pulses; phase coherence being maintained between repeated terahertz (THz) chirp pulses; and
detecting THz signals generated by coupling the phase coherent THz chirp pulse to a sample;
the detection being phase coherent; the phase coherent terahertz (THz) chirp pluses being phase coherent with a local oscillator included in a receiver used in detection; the local oscillator and a terahertz (THz) chirp pulse being phase locked using a frequency standard reference; repeated chirped pulse measurements being phase coherent;
maintained phase coherence enabling coherently averaging/subtracting of the generated THz signals.

30. The method of claim 29 wherein phase coherence is maintained by using a frequency standard reference in generating the phase coherent chirp pulses and to phase lock a local oscillator used in phase coherent heterodyne detection.

* * * * *

UNITED STATES PATENT AND TRADEMARK OFFICE
CERTIFICATE OF CORRECTION

| | | |
|---|---|---|
| PATENT NO. | : 8,748,822 B1 | Page 1 of 1 |
| APPLICATION NO. | : 13/346999 | |
| DATED | : June 10, 2014 | |
| INVENTOR(S) | : Eyal Gerecht et al. | |

It is certified that error appears in the above-identified patent and that said Letters Patent is hereby corrected as shown below:

In the Claims:

In column 14, line 16, "to detect RD over a frequency" should read -- to detect FID over a frequency --

Signed and Sealed this
Twelfth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,748,822 B1
APPLICATION NO. : 13/346999
DATED : June 10, 2014
INVENTOR(S) : Eyal Gerecht et al.

It is certified that error appears in the above-identified patent and that said Letters Patent is hereby corrected as shown below:

On the title page, under Item [73], Assignee, "University of Massachusetts, Boston, MA (US)" should read -- University of Massachusetts, Boston, MA (US) and Government of the United States of America, as represented by the Secretary of Commerce, the National Institute of Standards and Technology, Gaithersburg, MD (US) --

Signed and Sealed this
Third Day of March, 2015

Michelle K. Lee
*Deputy Director of the United States Patent and Trademark Office*